United States Patent
Castellaccio

(10) Patent No.: US 12,329,834 B2
(45) Date of Patent: Jun. 17, 2025

(54) ORAL CARE PRODUCT

(71) Applicant: Restituta Castellaccio, Saronno (IT)

(72) Inventor: Restituta Castellaccio, Saronno (IT)

( * ) Notice: Subject to any disclaimer, the term of this patent is extended or adjusted under 35 U.S.C. 154(b) by 0 days.

(21) Appl. No.: 18/842,405

(22) PCT Filed: Mar. 2, 2023

(86) PCT No.: PCT/EP2023/055265
§ 371 (c)(1),
(2) Date: Aug. 29, 2024

(87) PCT Pub. No.: WO2023/166108
PCT Pub. Date: Sep. 7, 2023

(65) Prior Publication Data
US 2025/0107985 A1    Apr. 3, 2025

(30) Foreign Application Priority Data
Mar. 2, 2022  (IT) .......................... 102022000003869

(51) Int. Cl.
*A61K 8/43* (2006.01)
*A61K 8/46* (2006.01)
*A61K 8/60* (2006.01)
*A61Q 11/00* (2006.01)

(52) U.S. Cl.
CPC .................. *A61K 8/43* (2013.01); *A61K 8/46* (2013.01); *A61K 8/606* (2013.01); *A61Q 11/00* (2013.01); *A61K 2800/92* (2013.01)

(58) Field of Classification Search
CPC . A61Q 11/00; A61K 8/23; A61K 8/44; A61K 8/67
USPC .................................................... 424/49, 401
See application file for complete search history.

(56) References Cited

FOREIGN PATENT DOCUMENTS

| EP | 2614812 A1 | 7/2013 |
| WO | 2020178148 A1 | 9/2020 |

OTHER PUBLICATIONS

Al-Kamel et al., "Subgingival microbiome of experimental gingivitis: shifts associated with the use of chlorhexidine and N-acetyl cysteine mouthwashes." Journal of Oral Microbiology 2019, vol. 11, 1608141. (Year: 2019).*
Cortellini et al., "Chlorhexidine with an anti discoloration system after periodontal flap surgery: a cross-over, randomized, triple-blind clinical trial." Journal of Clinical Periodontology, vol. 35, Issue 7: Jul. 2008; pp. 614-620 (Year: 2008).*
Al-Kamel A et al., "N-acetyl cysteine versus chlorexidine mouthwashes in prevention and treatment of experimental gingivitis: a randomized triple-blind, placebo-controlled clinical trial", Clinical Oral Investigations, vol. 23, No. 10, Jan. 23, 2019, pp. 3833-3842.
International Preliminary Report on Patentability of PCT/EP2023/055265 issued Jan. 30, 2024.
Search Report and Written Opinion of PCT/EP2023/055265 issued Jun. 6, 2023.

* cited by examiner

*Primary Examiner* — Walter E Webb
(74) *Attorney, Agent, or Firm* — Silvia Salvadori, P.C.; Silvia Salvadori

(57) ABSTRACT

The present invention relates to the use of N-acetyl cysteine to increase the effect of alkali or alkaline earth metal metabisulfite salts and ascorbic acid in counteracting pigmentation of tooth surfaces, dental mucous membranes, dental restorations or dental restorations in patients treated with chlorhexidine, and an oral care product comprising chlorhexidine, at least one metabisulfite salt of an alkali or alkaline earth metal, ascorbic acid, and N-acetyl cysteine.

14 Claims, 9 Drawing Sheets

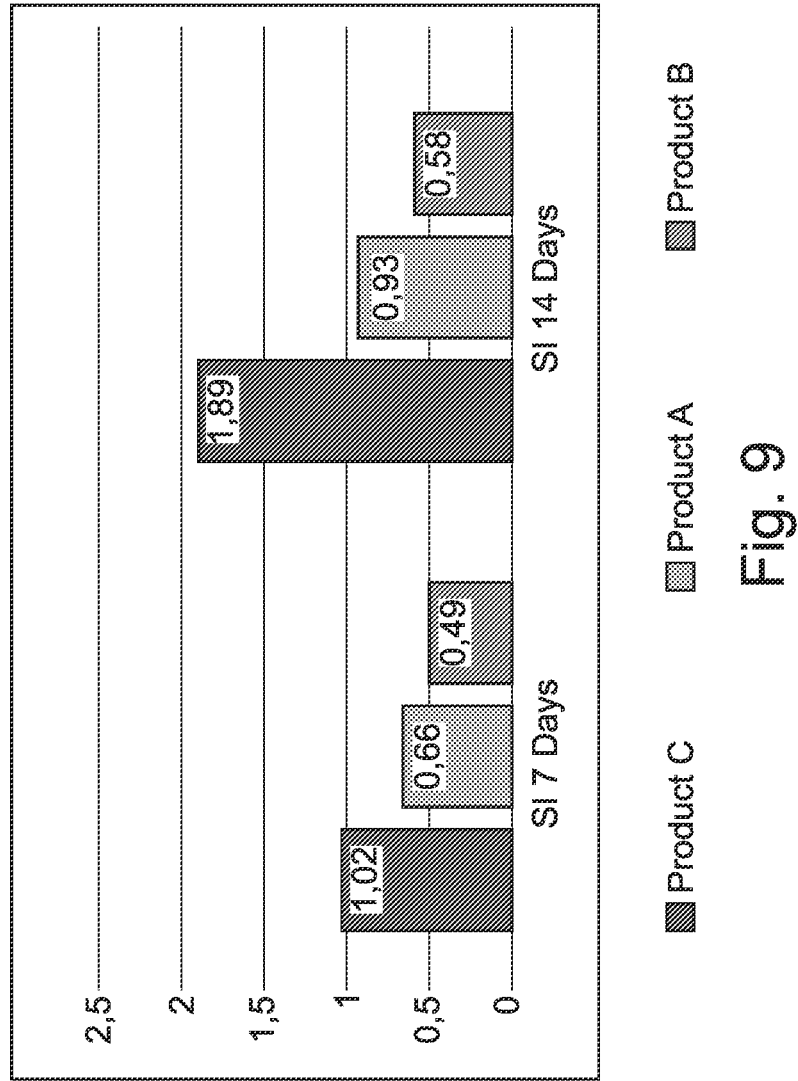

ORAL CARE PRODUCT

This application is a U.S. national stage of PCT/EP2023/055265 filed 2 Mar. 2023, which claims priority to and the benefit of Italian Application No. 102022000003869 filed 2 Mar. 2022, the contents of which are incorporated herein by reference in their entireties.

Field of the Invention

The present invention concerns the use of N-acetyl cysteine to increase the effect of metabisulfite salts of alkali or alkaline earth metals and ascorbic acid in counteracting tooth pigmentation in patients undergoing chlorhexidine treatment, as well as an oral care product comprising chlorhexidine, at least one metabisulfite salt of an alkali or alkaline earth metal, ascorbic acid, and N-acetyl cysteine.

Background Art

Chemical dental plaque control is one of the most important steps during many dental treatments as well as during normal home oral hygiene manoeuvres. For this purpose, many active ingredients have been produced and marketed, mostly in the form of mouthwashes, toothpastes or sprays, among which we can mainly mention chlorhexidine, essential oils, fluorine derivatives, delmopinol. However, from the data that have emerged from the literature in recent years, chlorhexidine still represents today the most effective product in the chemical plaque control, so much so that it is rightly defined as the active ingredient of reference.

Chlorhexidine is a molecule belonging to the bis-guanide family, and is known for its remarkable activity in the chemical plaque and gingivitis control. Although in relation to the intrinsic characteristics of the different bacterial species, it is in fact known that it has a bacteriostatic type action when used at low concentrations, while it has a mostly bactericidal effect, when used at higher concentrations. Chlorhexidine develops its own antiseptic effect thanks to the ability to establish chemical bonds with anionic groups (phosphate, sulfate, carboxyl group) present at the level of the bacterial cell wall and thus induce a marked increase in cell permeability and an alteration of the osmotic balance.

By virtue of its cationic properties, chlorhexidine is also known to bind:
  to oral mucous membranes,
  to the enamel hydroxyapatite,
  to the secondary film present on the dental surface,
  to salivary proteins, and
  to the bacteria and to the cellular polysaccharides of bacterial origin.

When bound to these oral structures, chlorhexidine can be slowly released while maintaining effective concentrations on microorganisms for about 8-18 hours. This effect that allows the active ingredient to remain at effective concentrations even hours after its administration is called substantivity and represents the strength of this active ingredient.

Despite the numerous advantages of chlorhexidine in terms of pharmacological activity, this active ingredient is also known to have some annoying side effects. Among the main known side effects, the most common one is certainly represented by the brownish pigmentations, which occur on dental surfaces and mucous membranes, especially resinous restorations or prosthetic products and therefore limit a long-term use thereof. In particular, it is believed that the bond between pigments and hydroxyapatite would be mediated by the interaction between the anionic groups of the dye molecules and the cationic ones of chlorhexidine, which once they are bonded would create a brownish film that is quite difficult to remove by simple brushing.

This side effect mainly occurs after a prolonged use of chlorhexidine, especially with formulations with a higher chlorhexidine concentration (0.2% or even 1% in some oral gels).

Anti-staining additives having the purpose of counteracting this side effect of the oral care products containing chlorhexidine are known. Among these additives, the ADS system, composed of ascorbic acid and sodium metabisulfite, is known to be able to lead to a lesser formation of tooth pigmentations without compromising the antiseptic benefits of chlorhexidine (Cortellini P, Labriola A, Zambelli R, Pini Prato G P, Nieri M, Tonetti M: Chlorhexidine with an anti-discoloration system after periodontal flap surgery: a cross-over, randomized, triple-blind clinical trial. Journal of Clinical Periodontology. 35, 7:614. 200).

The Applicant has found that, although the ADS system composed of ascorbic acid and sodium metabisulfite demonstrates an evident and appreciable efficacy in counteracting the pigmentation of the surfaces, mucous membranes, restorations, and dental prosthetic products in patients undergoing chlorhexidine treatment without compromising the antiseptic efficacy thereof, there remains a need to enhance the anti-pigmentation effect of the system ADS, especially for long-term treatments.

SUMMARY OF THE INVENTION

Aim of the present invention is therefore to improve and enhance the effect of the metabisulfite salts of alkali or alkaline earth metals and of ascorbic acid in counteracting the pigmentation (or staining) of the surfaces, mucous membranes, restorations, and dental prosthetic products in patients undergoing chlorhexidine treatment, without compromising the antiseptic efficacy of chlorhexidine itself, especially for long-term treatments.

According to the present invention, the Applicant has surprisingly found that this result is made possible by using, in combination with metabisulfite salts of alkali or alkaline earth metals and ascorbic acid, N-acetyl cysteine, which has been shown to be able to increase the effect of metabisulfite salts of alkali or alkaline earth metals and of ascorbic acid in counteracting the pigmentation of surfaces, mucous membranes, restorations, and dental prosthetic products in patients undergoing chlorhexidine treatment.

Therefore, the present invention concerns in a first aspect thereof N-acetyl cysteine for use in a method for treating the side effects of chlorhexidine in a patient undergoing chlorhexidine treatment, wherein said side effects involve a pigmentation of dental surfaces, dental mucous membranes, dental restorations, or dental prosthetic products of said patient, wherein said N-acetyl cysteine increases the effect of at least one metabisulfite salt of an alkali or alkaline earth metal and of ascorbic acid in counteracting said pigmentation of dental surfaces, dental mucous membranes, dental restorations, or dental prosthetic products. It has been surprisingly found that the association of N-acetyl cysteine with a metabisulfite salt of an alkali or alkaline earth metal and ascorbic acid increases its contrast effect of the pigmentation/staining of the surfaces, mucous membranes, restorations, and dental prosthetic products due to chlorhexidine, without compromising the antiseptic efficacy of chlorhexidine itself, even for long-term treatments.

Thanks to the specific combination of N-acetyl cysteine, at least one metabisulfite salt of an alkali or alkaline earth metal and of ascorbic acid and chlorhexidine, it is therefore possible to provide an oral care product that has therefore a range of properties capable of improving the properties of oral care products based on the system ADS, thus expanding its application possibilities.

In a further aspect, the present invention therefore also concerns an oral care product comprising chlorhexidine, at least one metabisulfite salt of an alkali or alkaline earth metal, ascorbic acid, and N-acetyl cysteine.

Thanks to the presence of N-acetyl cysteine, of at least one metabisulfite salt of an alkali or alkaline earth metal and of ascorbic acid, the product according to the present invention based on chlorhexidine is effective against pathologies of the oral cavity, in particular of the bacterial plaque, without giving rise to, or strongly limiting, the side effects of the prolonged use of said active component which entail a pigmentation of the surfaces, mucous membranes, restorations, and dental prosthetic products.

Thus, in a further aspect thereof the present invention refers to an oral care product comprising chlorhexidine, at least one metabisulfite salt of an alkali or alkaline earth metal, ascorbic acid, and N-acetyl cysteine, for use in the treatment of bacterial plaque in a patient in need thereof.

The Applicant has in fact found that the use of N-acetyl cysteine according to the present invention, by improving and enhancing the effect of the metabisulfite salts of alkali or alkaline earth metals and of ascorbic acid in counteracting the pigmentation of the surfaces, mucous membranes, restorations, and dental prosthetic products in patients undergoing anti-plaque treatment with chlorhexidine constitutes an innovative aspect of particular value of said oral care product.

BRIEF DESCRIPTION OF THE DRAWINGS

In the drawings:

FIG. 9 shows the results of the 7- and 14-day Stain Index (SI) test for the groups that used products A, B, and C according to Example 3. The three groups show a different trend. The pigmentation caused by the traditional mouthwash at 14 days is more than double that of the ADS mouthwashes. The ADS mouthwashes show significant differences with the "control" mouthwash (CHX, Group C) statistically significant both at T=7 days and at T=14 days. Group B (CHX-ADS-NAC) shows significantly lower SI values also than group A (CHX-ADS) at T=14 days.

DETAILED DESCRIPTION OF THE INVENTION

Figure 1:
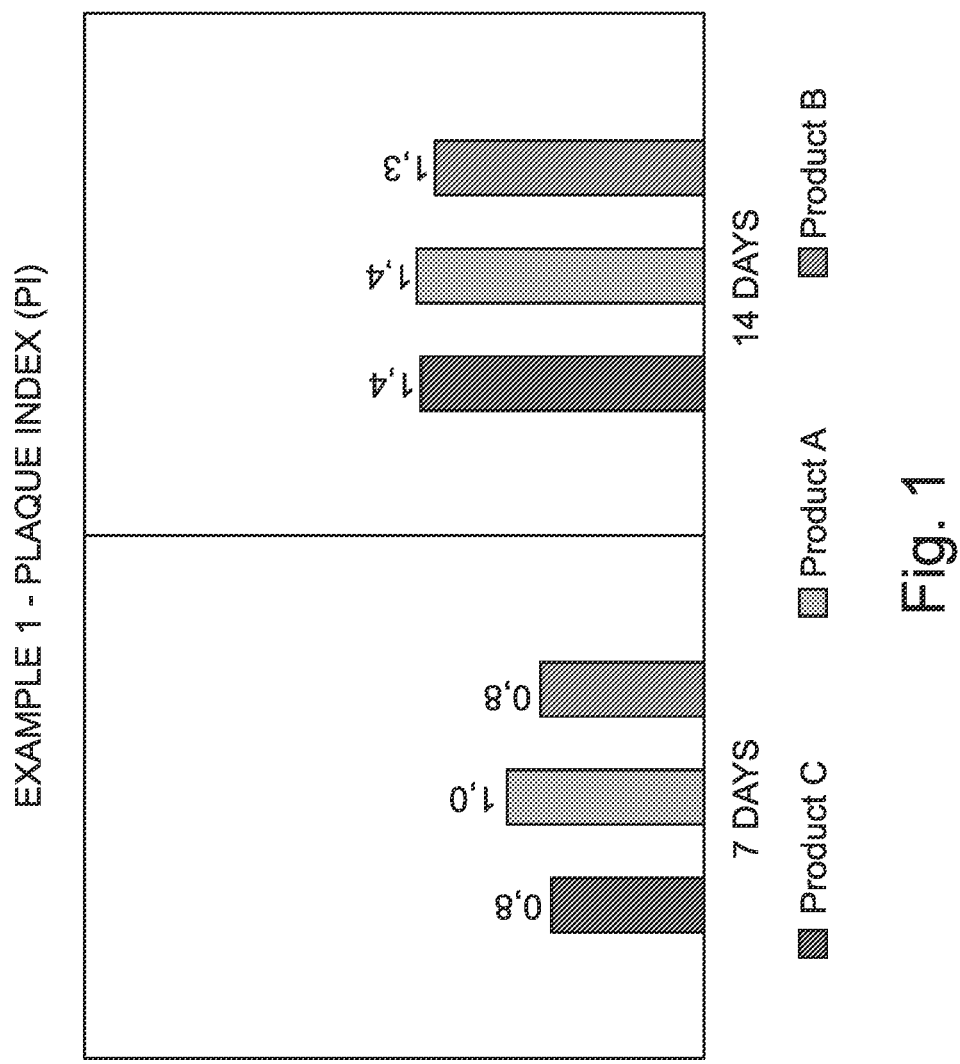
FIG. 1 shows the 7- and 14-day Plaque Index (PI) test results for the groups that used products A, B, and C according to Example 1.

The present invention concerns in a first aspect thereof the use of N-acetyl cysteine in a method for treating the side effects of chlorhexidine in a patient undergoing chlorhexidine treatment, wherin said side effects involve a pigmentation of dental surfaces, dental mucous membranes, dental restorations, or dental prosthetic products of said patient, wherein said N-acetyl cysteine increases the effect of at least one metabisulfite salt of an alkali or alkaline earth metal and of ascorbic acid in counteracting said pigmentation of dental surfaces, dental mucous membranes, dental restorations, or dental prosthetic products. The Applicant has in fact surprisingly found that it is possible to improve and enhance the effect of the metabisulfite salts of alkali or alkaline earth metals and of ascorbic acid in counteracting the pigmentation/staining of surfaces, mucous membranes, restorations, and dental prosthetic products in patients undergoing chlorhexidine treatment, without compromising the antiseptic efficacy of chlorhexidine itself, using, in combination with them N-acetyl cysteine, which has been shown to be able to increase the contrast effect of said pigmentation. Thanks to the specific combination of N-acetyl cysteine, at least one metabisulfite salt of an alkali or alkaline earth metal and of ascorbic acid and chlorhexidine, it is therefore possible to provide an oral care product that has therefore a range of properties capable of improving the properties of oral care products based on the ADS system, thus expanding its application possibilities.

In a further aspect, the present invention therefore also concerns an oral care product comprising chlorhexidine, at least one metabisulfite salt of an alkali or alkaline earth metal, ascorbic acid, and N-acetyl cysteine.

The present invention can present in one or more of its aspects or one or more of the preferred characteristics reported below, which can be combined with one another as preferred according to the application requirements.

Within the context of the present description and following claims, all the numerical magnitudes indicating quantities, parameters, percentages, and so on are to be considered preceded in every circumstance by the term "about" unless indicated otherwise. Further, all the ranges of numerical magnitudes include all the possible combinations of maximum and minimum numerical values and all the possible intermediate ranges, as well as those indicated below.

In the present invention the expression:
"% by weight with respect to the total volume" of a product, for example a mouthwash, means the amount in grams of a given component present in 100 millilitres (mL) of said product; and "chlorhexidine" means, unless otherwise specified, the compound 1,1'-hexamethylenebis [5-(p-chlorphenyl) biguanide], a salt thereof or a complex thereof.

Preferably, in the oral care product, chlorhexidine is in the form of a salt or a complex. As chlorhexidine salt, for example, chlorhexidine digluconate or chlorhexidine diacetate can be used in the mouthwash according to the present invention. Preferably, the oral care product according to the present invention comprises chlorhexidine in the form of chlorhexidine gluconate.

Preferably, the oral care product further comprises sodium DNA. "Sodium DNA" in the present invention means the sodium salt of deoxyribonucleic acid, for example obtainable by extraction of native deoxyribonucleic acid from gonad tissue of male sturgeon and subsequently purified, depolymerized and neutralized with sodium ions.

Sodium DNA suitable for the purposes of the present invention is commercially available, for example the one sold under the name Kalinat A W powder (Kalichem). Said amount of sodium DNA has in fact proved to be optimal for counteracting the irritating effect of chlorhexidine on the oral mucous membranes, exerting a protective effect on them and a healing effect on possible wounds of the oral cavity, thus also favouring a correct trophism of the oral mucous membranes themselves.

In a preferred embodiment thereof, said oral care product is selected from the group consisting of: mouthwash, periodontal gel, and toothpaste.

In a first preferred embodiment thereof, therefore, the oral care product according to the present invention is a mouthwash.

Preferably, said mouthwash comprises chlorhexidine in an amount ranging from 0.01% to 0.30% by weight, more preferably from 0.05% to 0.30% by weight, even more preferably from 0.09% to 0.20% by weight, with respect to the total volume of the mouthwash.

The mouthwash according to the present invention also comprises at least one metabisulfite salt of an alkali or alkaline earth metal.

The presence of at least one metabisulfite salt of an alkali or alkaline earth metal counteracts the drawback of dark pigmentation on the teeth, a side effect of chlorhexidine.

Preferably, the at least one metabisulfite salt of an alkali or alkaline earth metal is selected from the group consisting of: sodium metabisulfite, potassium metabisulfite, calcium metabisulfite. More preferably, the mouthwash according to the present invention comprises sodium metabisulfite.

Preferably, in the mouthwash according to the present invention the amount of the at least one metabisulfite salt of an alkali or alkaline earth metal ranges from 0.1% to 0.5%, more preferably from 0.15% to 0.3% by weight with respect to the total volume of the mouthwash.

The mouthwash according to the present invention further comprises ascorbic acid.

Preferably, in the mouthwash according to the present invention the amount of ascorbic acid ranges from 0.1% to 1.0% by weight, with respect to the total volume of the mouthwash.

The presence of ascorbic acid also counteracts the drawback of dark pigmentation on the teeth, a side effect of chlorhexidine.

Preferably, the mouthwash according to the present invention comprises ascorbic acid and at least one metabisulfite salt of an alkali or alkaline earth metal, even more preferably from 0.1% to 0.5% by weight of at least one metabisulfite salt of an alkali or alkaline earth metal and from 0.1% to 1.0% by weight of ascorbic acid, with respect to the total volume of the mouthwash.

Said combination of components in these amounts has already proved particularly effective in counteracting the side effect of chlorhexidine of dark pigmentation on the teeth, and is the basis of the system ADS.

The mouthwash according to the present invention further comprises N-acetyl cysteine.

N-acetyl cysteine, as will also be demonstrated in the experimental part, has been shown to be able to increase the effect of the metabisulfite salts of alkali or alkaline earth metals and of ascorbic acid, in counteracting the drawback of brown pigmentation of the surfaces, mucous membranes, restorations, and dental prosthetic products in patients undergoing chlorhexidine treatment.

Preferably, in the mouthwash according to the present invention the amount of N-acetyl cysteine ranges from 0.01% to 1.0%, more preferably from 0.2% to 0.7%, by weight with respect to the total volume of the mouthwash.

In addition to the above-mentioned components, the mouthwash according to the present invention preferably comprises tribasic sodium citrate.

Preferably, in the mouthwash according to the present invention the amount of tribasic sodium citrate ranges from 0.8% to 2.0%, more preferably from 0.8% to 1.2%, by weight with respect to the total volume of the mouthwash.

The presence of tribasic sodium citrate in said amounts advantageously allows regulating the pH of the mouthwash to optimal values for its use.

In a preferred embodiment, the mouthwash according to the present invention comprises ascorbic acid and tribasic sodium citrate. More preferably, the mouthwash according to the present invention comprises from 0.1% to 1% by weight with respect to the total volume of the ascorbic acid in the mouthwash and from 0.8% to 2.0% by weight with respect to the total volume of the tribasic sodium citrate mouthwash.

It has in fact surprisingly been discovered that said combination of ascorbic acid and tribasic sodium citrate allows stabilizing the formulation of the mouthwash according to the present invention.

Preferably, the mouthwash according to the present invention comprises at least one polyvinyl pyrrolidone-vinyl acetate copolymer. Polyvinyl pyrrolidone-vinyl acetate copolymers suitable for the purposes of the present invention are commercially available, for example those marketed under the name Luviskol® (BASF SE).

The at least one polyvinyl pyrrolidone-vinyl acetate copolymer advantageously exerts a film-forming and anti-plaque action in the mouthwash according to the present invention.

Preferably, in the mouthwash according to the present invention the amount of the at least one polyvinyl pyrrolidone-vinyl acetate copolymer ranges from 0.05% to 1%, more preferably from 0.3% to 1%, by weight with respect to the total volume of the mouthwash.

Preferably, said mouthwash also comprises sodium DNA.

Sodium DNA advantageously exerts a protective and healing effect on oral mucous membranes further limiting some of the side effects of prolonged use of chlorhexidine-based oral care products, which include alterations in cell structure, including vacuolation, degeneration of the cell nucleus, and enlargement of intercellular spaces.

Preferably, in the mouthwash the amount of sodium DNA ranges from 0.01% to 0.2%, more preferably from 0.05% to 0.1%, by weight with respect to the total volume of the mouthwash.

In a preferred embodiment thereof, the oral care product according to the present invention is a mouthwash comprising from 0.01% to 0.30% by weight of chlorhexidine, from 0.1% to 0.5% by weight of at least one metabisulfite salt of an alkali or alkaline earth metal, from 0.1% to 1.0% by weight of ascorbic acid, from 0.01% to 1.0%, more preferably from 0.2% to 0.7%, by weight of N-acetyl cysteine, from 0.01% to 0.2%, more preferably from 0.01% to 0.1%, by weight of sodium DNA from 0.05% to 1%, more preferably from 0.3% to 1%, by weight of at least one polyvinyl pyrrolidone-vinylacetate copolymer, with respect to the total volume of the mouthwash.

The mouthwash according to the invention may contain one or more of the other possible ingredients known in the art for oral hygiene solutions.

In particular, the mouthwash according to the present invention can further comprise one or more additives selected from the group consisting of:

sweeteners, flavourings, wetting agents, preservatives, emulsifiers, pH regulators, food colourings.

As sweeteners, the mouthwash according to the present invention can for example comprise xylitol, sodium saccharinate, potassium acesulfame, sucralose, stevia extract.

As flavourings, the mouthwash according to the present invention can for example comprise peppermint, menthol, anethole, *Mentha viridis*, cinnamon, cloves, eucalyptol.

As wetting agents, the mouthwash according to the present invention can for example comprise propylene glycol, sorbitol, glycerin As preservatives, the mouthwash according to the present invention can for example comprise sodium benzoate, methylisothiazolinone.

As solubilizing surfactants, the mouthwash according to the present invention can for example comprise: hydrogenated castor oil Peg 40, Poloxamer 407.

As pH regulators, the mouthwash according to the present invention can for example comprise sodium citrate, citric acid.

As colourings, the mouthwash according to the present invention can for example comprise CI 19140, CIU 42090, CI 17200.

The mouthwash according to the invention is conveniently prepared in a known way in the form of solution or suspension in a suitable solvent medium, preferably water.

According to a preferred embodiment, the mouthwash according to the invention comprises the following components:
1. Water
2. Xylitol
3. Propylene glycol
4. Hydrogenated castor oil PEG 40
5. Sodium acetate
6. Ascorbic acid
7. Chlorhexidine digluconate
8. Polyvinyl pyrrolidone-vinyl acetate copolymer
9. N-Acetyl cysteine
10. Sodium DNA
11. Flavouring
12. Poloxamer 407
13. Sodium metabisulfite
14. Sodium hydroxide
15. Sodium benzoate
16. Acetic acid According to a further preferred embodiment, the mouthwash according to the invention comprises the following components:
1. Water
2. Xylitol
3. Propylene glycol
4. Hydrogenated castor oil PEG 40
5. Ascorbic acid
6. Chlorhexidine digluconate
7. Polyvinyl pyrrolidone-vinyl acetate copolymer
8. N-Acetyl cysteine
9. Sodium DNA
10. Flavouring
11. Poloxamer 407
12. Sodium metabisulfite
13. Sodium citrate
14. Citric acid
15. C.I. 42090
16. C.I. 17200

In a further preferred embodiment, the oral care product according to the present invention is a periodontal gel.

According to a preferred embodiment, the periodontal gel according to the invention comprises the following components:
1. Water
2. Propylene glycol
3. Hydroxyethyl cellulose
4. Polyvinyl pyrrolidone-vinyl acetate copolymer
5. Hydrogenated castor oil PEG 40
6. Chlorhexidine digluconate
7. N-acetyl cysteine
8. Sodium acetate
9. Sodium DNA
10. Menthol
11. Peppermint oil
12. Acetic acid
13. Sodium metabisulfite
14. Ascorbic acid Preferably, the periodontal gel according to the present invention comprises from 0.5% by weight to 1.0% by weight of chlorhexidine, with respect to the total volume of the periodontal gel.

Preferably, the periodontal gel according to the present invention comprises from 0.01% to 1.0%, more preferably from 0.2% to 0.7% by weight of N-acetyl cysteine, with respect to the total volume of the periodontal gel.

Preferably, the periodontal gel according to the present invention comprises sodium DNA, even more preferably in amounts of at most 0.3%, more preferably from 0.01% to 0.3%, by weight with respect to the total weight of the periodontal gel.

As already stated with respect to the mouthwash according to the present invention, sodium DNA advantageously exerts a protective and healing effect on oral mucous membranes further limiting some of the side effects of prolonged use of chlorhexidine-based oral care products, including alterations of cell structure, including vacuolation, degeneration of the cell nucleus, and widening of intercellular spaces.

In a still further preferred embodiment, the oral care product according to the present invention is a toothpaste.

According to a preferred embodiment, the toothpaste according to the invention comprises the following components:
1. Sorbitol
2. Water
3. Silica (Hydrated silica)
4. Glycerol
5. Xylitol
6. Cocamidopropyl betaine
7. Polyvinyl pyrrolidone-vinyl acetate copolymer
8. Hydrogenated castor oil PEG 40
9. N-acetyl cysteine
10. Flavouring
11. Chlorhexidine digluconate
12. Carboxymethyl cellulose
13. Ascorbic acid
14. Sodium metabisulfite
15. Sodium DNA
16. Sodium saccharin
17. Sodium benzoate
18. Sodium citrate Preferably, the toothpaste according to the present invention comprises from 0.05% by weight to 0.2% by weight of chlorhexidine, with respect to the total volume of the toothpaste.

Preferably, the toothpaste according to the present invention comprises ascorbic acid and at least one metabisulfite salt of an alkali or alkaline earth metal, even more preferably from 0.1% to 0.5% by weight of at least one metabisulfite salt of an alkali or alkaline earth metal and from 0.1% to 1.0% by weight of ascorbic acid, with respect to the total volume of the toothpaste.

As already stated with respect to the mouthwash and to the periodontal gel according to the present invention, said combination of components is already particularly effective for counteracting the side effect of chlorhexidine of dark pigmentation on the teeth, and is the basis of the ADS system.

Preferably, the toothpaste according to the present invention comprises from 0.01% to 1.0%, more preferably from 0.2% to 0.7% by weight of N-acetyl cysteine, with respect to the total volume of the toothpaste.

Preferably, at least one inorganic fluoride can optionally be present in the toothpaste according to the invention.

Preferably, in the toothpaste according to the present invention the amount of sodium DNA ranges from 0.01% to 0.05% by weight with respect to the total volume of the toothpaste.

As already stated with respect to the mouthwash according to the present invention, sodium DNA advantageously exerts a protective and healing effect on oral mucous membranes further limiting some of the side effects of prolonged use of chlorhexidine-based oral care products, including alterations of cell structure, including vacuolation, degeneration of the cell nucleus, and widening of intercellular spaces.

Thanks to the presence of N-acetyl cysteine, of at least one metabisulfite salt of an alkali or alkaline earth metal and of ascorbic acid, the product according to the present invention based on chlorhexidine is effective against pathologies of the oral cavity, in particular of the bacterial plaque, without giving rise to, or strongly limiting, the side effects of the prolonged use of said active component which entail a pigmentation of the surfaces, mucous membranes, restorations, and dental prosthetic products.

Thus, in a further aspect thereof the present invention refers to an oral care product comprising chlorhexidine, at least one metabisulfite salt of an alkali or alkaline earth metal, ascorbic acid, and N-acetyl cysteine, for use in the treatment of bacterial plaque in a patient in need thereof.

The Applicant has in fact found that the use of N-acetyl cysteine according to the present invention, by improving and enhancing the effect of the metabisulfite salts of alkali or alkaline earth metals and of ascorbic acid in counteracting the pigmentation of the surfaces, mucous membranes, restorations, and dental prosthetic products in patients undergoing anti-plaque treatment with chlorhexidine constitutes an innovative aspect of particular value of said oral care product.

Thus, in a preferred aspect thereof, the present invention refers to the use of N-acetyl cysteine in a patient undergoing chlorhexidine treatment according to the first aspect of the invention, and wherein said chlorhexidine treatment is carried out with an oral care product according to the present invention.

EXPERIMENTAL PART

The invention is now illustrated by means of some Examples to be understood for illustrative and non-limiting purposes.

Example 1

Goal of the Study

The aim of this study was to evaluate the efficacy of a 0.2% chlorhexidine mouthwash containing 0.01% by weight of sodium DNA and the anti-pigmentation ADS system (0.5% by weight of sodium metabisulfite, 0.5% by weight of ascorbic acid) and compare it with a mouthwash having the same composition but with an additional 0.5% by weight of N-acetyl cysteine. As a control group, a traditional mouthwash was used with 0.2% chlorhexidine, but without sodium metabisulfite, ascorbic acid, sodium DNA, or N-acetyl cysteine.

Materials and Methods

For this study, 15 male and female healthy volunteers, aged 19-29 years, were selected in accordance with the principles of the Helsinki Declaration. Patients with serious systemic diseases, such as cardiovascular disease, diabetes, neurological or psychiatric syndromes, or infectious diseases, were not included in the trial. Also excluded from the study were patients who were unable to correctly perform home oral hygiene manoeuvres, patients suffering from chronic periodontal disease with pockets>4 mm, subjects with fewer than 20 elements in the dental arch.

After enrolment, 3 types of bottles were prepared for each patient, which were absolutely identical, inert, opaque, with a capacity of 250 ml, into which it was introduced:

Product A: mouthwash with chlorhexidine at 0.2% by weight containing 0.5% by weight of sodium metabisulfite, 0.5% by weight of ascorbic acid, and 0.01% by weight of sodium DNA, with respect to the total volume of the mouthwash;

Product B: like Product A, but with the addition of 0.5% by weight of N-acetyl cysteine, with respect to the total volume of the mouthwash; and Product C: traditional mouthwash with chlorhexidine at 0.2% by weight with respect to the total volume of the mouthwash.

The bottles, with a neutral label, were then simply marked with an alphanumeric code that uniquely identified the patient to whom it had been assigned. The reading key was kept unknown by the test organizer until the end of the evaluation, in order to prevent the volunteer patient or the operator selected for the evaluations from becoming aware of what type of mouthwash they were testing. The test was then performed according to the "double-blind" criterion. Prior to the start of the study, all patients underwent professional oral hygiene sessions, in order to remove existing soft and hard plaque deposits and to zero the periodontal indices to be analysed:

Plaque index (PI), for the amount of plaque present (Loe H., Silness J: Periodontal disease in pregnancy. Prevalence and severity. Acta odontologica *Scandinavica*. 1963; 21:533-551).

Gingival index (GI), for the level of gum inflammation (Silness J, Loe H: Periodontal disease in pregnancy. II. Correlation between oral hygiene and periodontal conditions. Acta odontologica *Scandinavica*. 1964; 22:121-135).

Stain index (SI), for the extent of pigmentations (Lobene R R: Effect of dentifrices on tooth stains with controlled brushing. J. Am. Dent. Assoc. 1968; 77:849-855, Soskolne W. A., Heasman P. A., Stabholz A., Smart G. J, Palmer M., Flashner M., Newman H. N.: Sustained Local Delivery of chlorexidine in the treatment of periodontitis: a multi-center study. J Clin Periodontol 1997; 68:32-38).

The 15 patients were divided into 3 groups identical in number and assigned to group A (Product A), to group B (Product B) or to group C (Product C) and each patient was then assigned 2 bottles of the corresponding product.

The patients performed a 14-day rinse cycle with the delivered product. The cycle included a rinse with 15 ml of pure product for one minute, to be performed 2 times a day. During the period of use of the mouthwashes, the patients did not brush or use any other oral hygiene devices. Finally, the patients were asked not to take substances capable of favouring the deposition of pigments, such as coffee, tea, red wine or cigarette smoke, less than an hour before or after rinsing and in any case to report their possible intake during the day by means of a special form to be filled out.

After 7 and 14 days the periodontal parameters PI and GI were then measured, in addition to the SI.

All the data were collected by a single examiner in special folders and then analysed through an analysis program and spreadsheet. The statistical analysis was performed by Student's T-Test for unpaired data.

Results

All 15 selected volunteer patients completed the study. There were no interruptions to the protocol nor delays in the evaluation sessions. The patients maintained similar dietary regimens during the treatment cycle to which they had been subjected, without substantial differences especially in the intake of the staining substances that they were asked to report on the appropriate sheet delivered.

Figure 2:
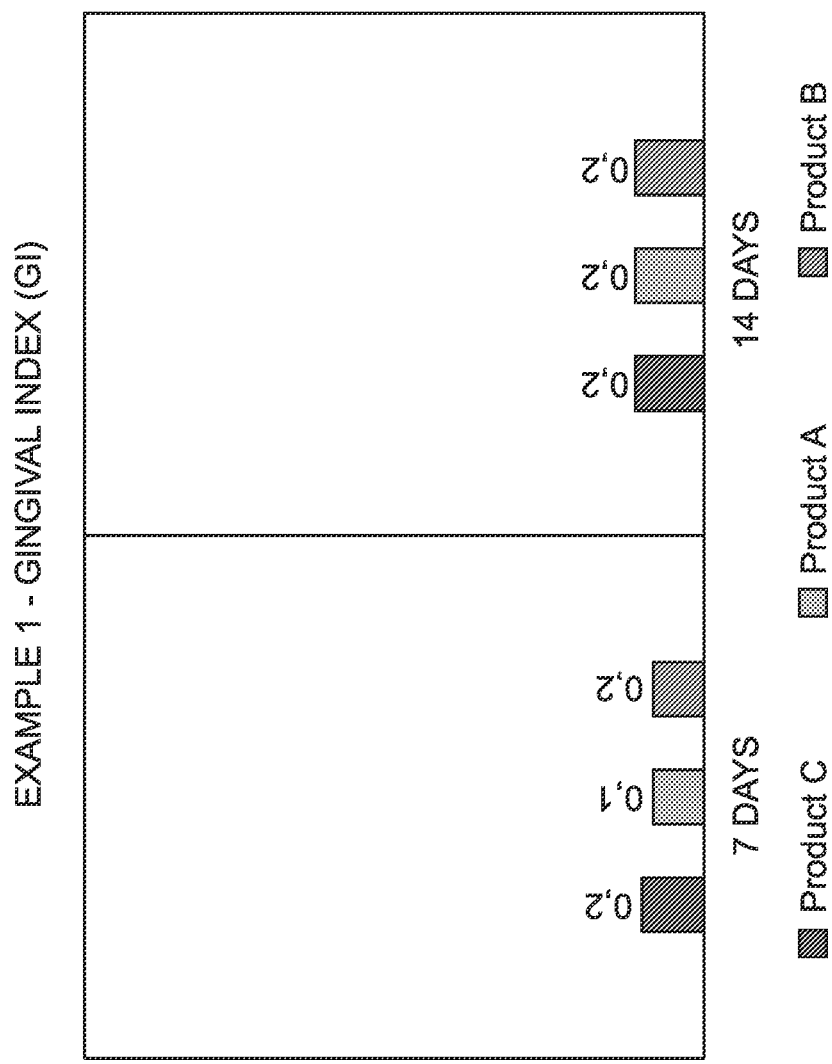
FIG. 2 shows the results of the 7- and 14-day Gingival Index (GI) test for the groups that used products A, B, and C according to Example 1.

In the measurements carried out, the Plaque Index, and Gingival Index values showed a similar trend with all types of mouthwashes (FIGS. 1 and 2). In particular, a progressive plaque accumulation on the tooth surfaces was highlighted in most cases. The evaluation of the amount of plaque with the aid of the periodontal probe showed in fact a mostly invisible accumulation in the first week (PI=0 or 1) and more visible in the second week (also PI=2).

Regarding the analysis of the Gingival Index, despite the plaque accumulation described above, particular inflammatory gingival states were not appreciated, except for soft gingival redness at a marginal level in a few subjects (GI=1). This confirmed the maintenance of the antiseptic efficacy of chlorhexidine in Products A and B, throughout the duration of the treatments, of significant duration.

Figure 3:
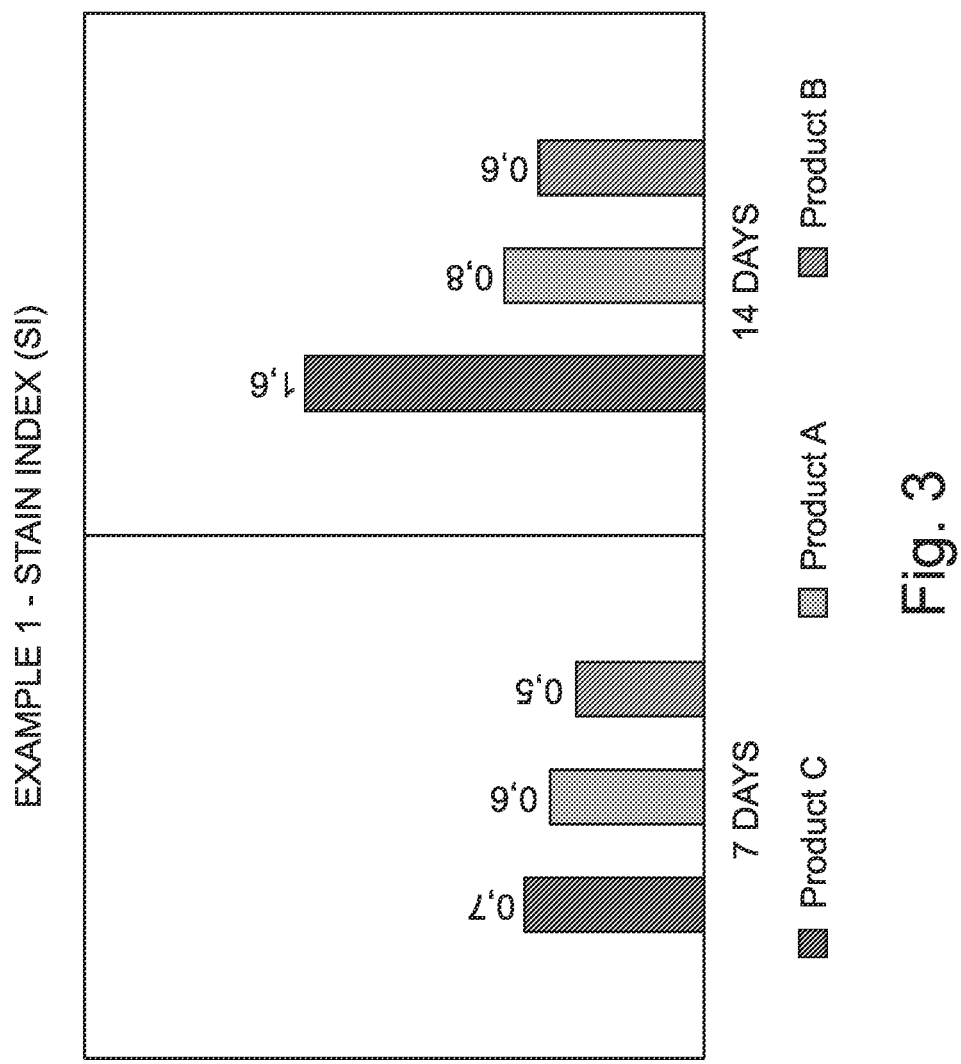
FIG. 3 shows the results of the 7- and 14-day Staining Index (SI) test for the groups that used products A, B, and C according to Example 1.

During the evaluation of the Stain Index (SI) the 3 mouthwashes instead showed different results in the development of dental pigmentation (FIG. 3).

The analysis relative to the average values showed a lower tendency to pigmentation of tooth surfaces after the treatment cycles with Products A and B, compared to those with control mouthwash (Product C). The difference, already present after 7 days, was particularly marked after 14 days of treatment for the groups treated with the products A B compared to the group treated with Product C.

In addition thereto, a tendency to develop a lower pigmentation at all in the group of patients treated with Product B was found, which allowed to highlight how the use of N-acetyl cysteine allows to increase the effect of the ADS system with sodium metabisulfite and ascorbic acid in counteracting tooth pigmentation in patients undergoing chlorhexidine treatment.

Example 2

Goal of the Study

The aim of this study was to evaluate the efficacy of a 0.2% chlorhexidine mouthwash and the anti-staining ADS system (0.5% by weight of sodium metabisulfite, 0.5% by weight of ascorbic acid) and compare it with a mouthwash having the same composition but with an additional 0.5% by weight of N-acetyl cysteine. As a control group, a traditional mouthwash was used with 0.2% chlorhexidine, but without sodium metabisulfite, ascorbic acid, or N-acetyl cysteine.

Materials and Methods

For this study, 18 male and female healthy volunteers, aged 21-33 years, were selected in accordance with the principles of the Helsinki Declaration. Patients with serious systemic diseases, such as cardiovascular disease, diabetes, neurological or psychiatric syndromes, or infectious diseases, were not included in the trial, as was done in the study in Example 1. Also excluded from the study were patients who were unable to correctly perform home oral hygiene manoeuvres, patients suffering from chronic periodontal disease with pockets>4 mm, subjects with fewer than 20 elements in the dental arch.

After enrolment, 3 types of bottles were prepared for each patient, which were absolutely identical, inert, opaque, with a capacity of 250 ml, into which it was introduced:

Product D: mouthwash with chlorhexidine at 0.2% by weight and containing 0.5% by weight of sodium metabisulfite and 0.5% by weight of ascorbic acid, with respect to the total volume of the mouthwash;

Product E: like Product D, but with the addition of 0.5% by weight of N-acetyl cysteine, with respect to the total volume of the mouthwash; and Product F: traditional mouthwash with chlorhexidine at 0.2% by weight with respect to the total volume of the mouthwash.

Like for Example 1, the bottles, with a neutral label, were then simply marked with an alphanumeric code that uniquely identified the patient to whom it had been assigned. The reading key was kept unknown by the test organizer until the end of the evaluation, in order to prevent the volunteer patient or the operator selected for the evaluations from becoming aware of what type of mouthwash they were testing. The test was then performed according to the "double-blind" criterion. Prior to the start of the study, all patients underwent professional oral hygiene sessions, in order to remove existing soft and hard plaque deposits and to zero the periodontal indices to be analysed: Plaque Index, Gingival Index, and Stain Index, according to the same methods used in Example 1.

The 18 patients were divided into 3 groups identical in number and assigned to group D (Product D), to group E (Product E) or to group F (Product F) and each patient was then assigned 2 bottles of the corresponding product.

The patients performed a 14-day rinse cycle with the delivered product. The cycle included a rinse with 15 ml of pure product for one minute, to be performed 2 times a day. During the period of use of the mouthwashes, the patients did not brush or use any other oral hygiene devices. Finally, the patients were asked not to take substances capable of favouring the deposition of pigments, such as coffee, tea, red wine or cigarette smoke, less than an hour before or after rinsing and in any case to report their possible intake during the day by means of a special form to be filled out.

After 7 and 14 days the periodontal parameters PI and GI were then measured, in addition to the SI.

All the data were collected by a single examiner in special folders and then analysed through an analysis program and spreadsheet. The statistical analysis was performed by Student's T-Test for unpaired data.

Results

All 18 selected volunteer patients completed the study. There were no interruptions to the protocol nor delays in the evaluation sessions. The patients maintained similar dietary regimens during the treatment cycle to which they had been subjected, without substantial differences especially in the intake of the staining substances that they were asked to report on the appropriate sheet delivered.

Figure 4:
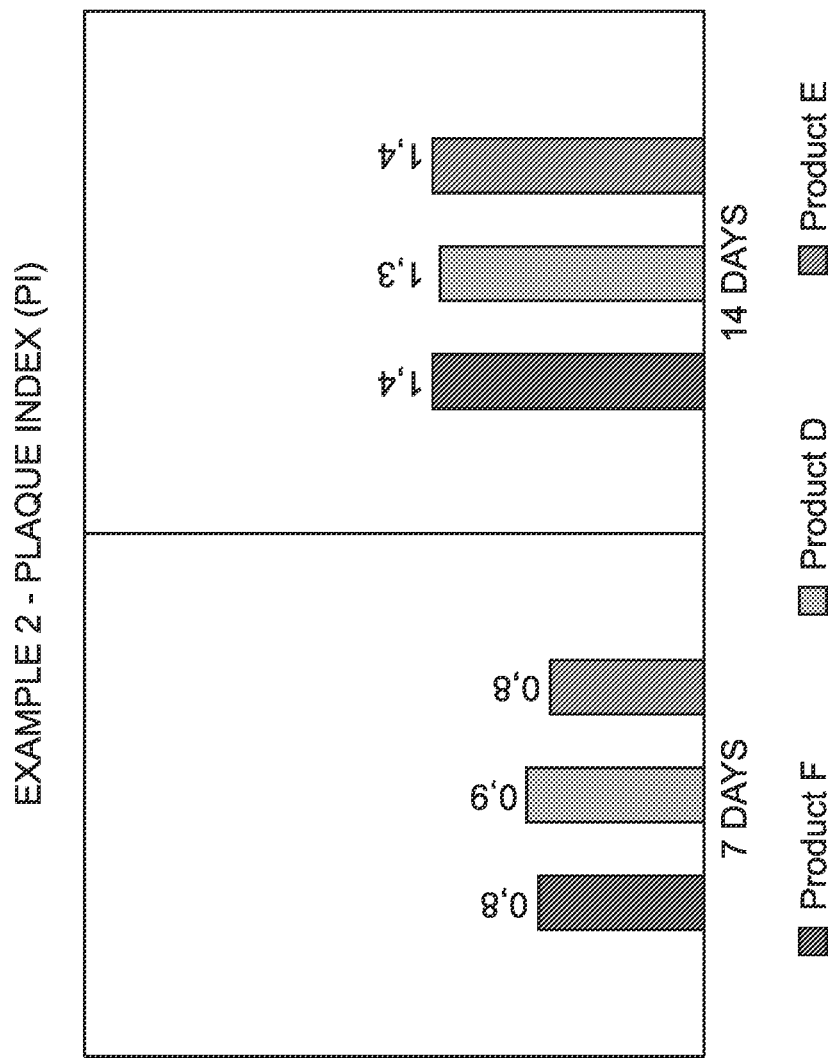
FIG. 4 shows the 7- and 14-day Plaque Index (PI) test results for the groups that used products D, E, and F according to Example 2.
Figure 5:
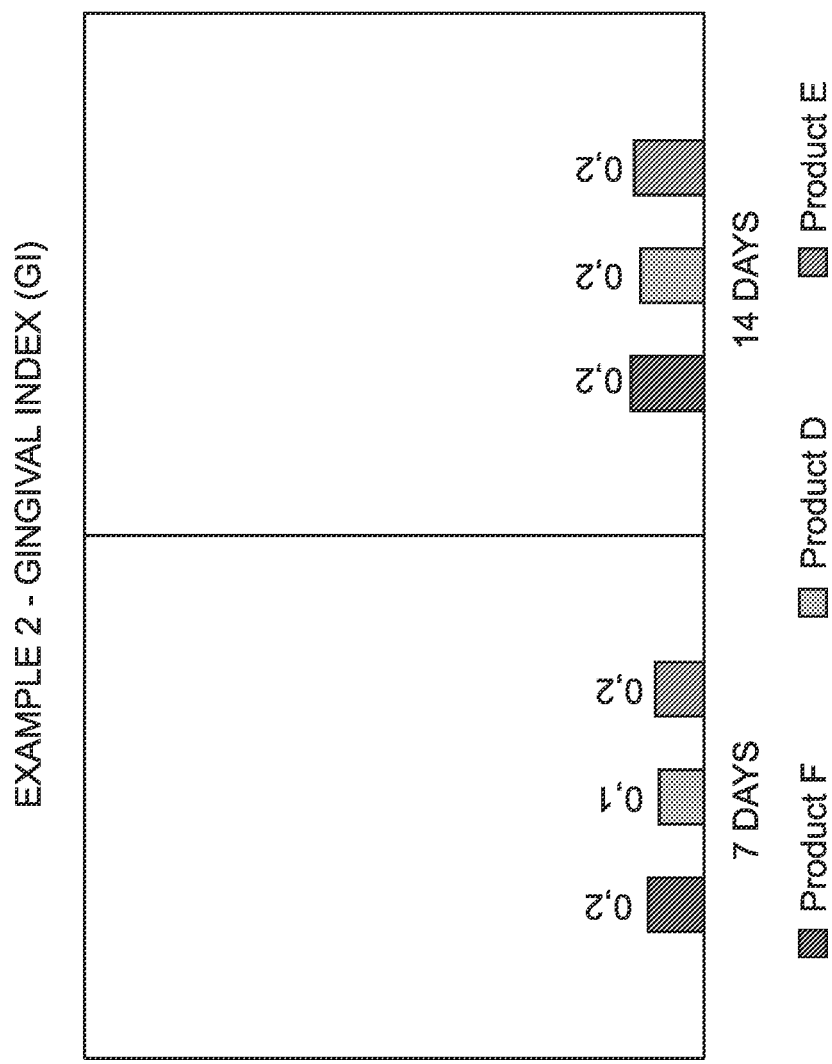
FIG. 5 shows the results of the 7- and 14-day Gingival Index (GI) test for the groups that used products D, E, and F according to Example 2.

In the measurements carried out, the Plaque Index, and Gingival Index values showed a similar trend with all types of mouthwashes (FIGS. 4 and 5), completely consistent with what was also highlighted in Example 1.

Figure 6:
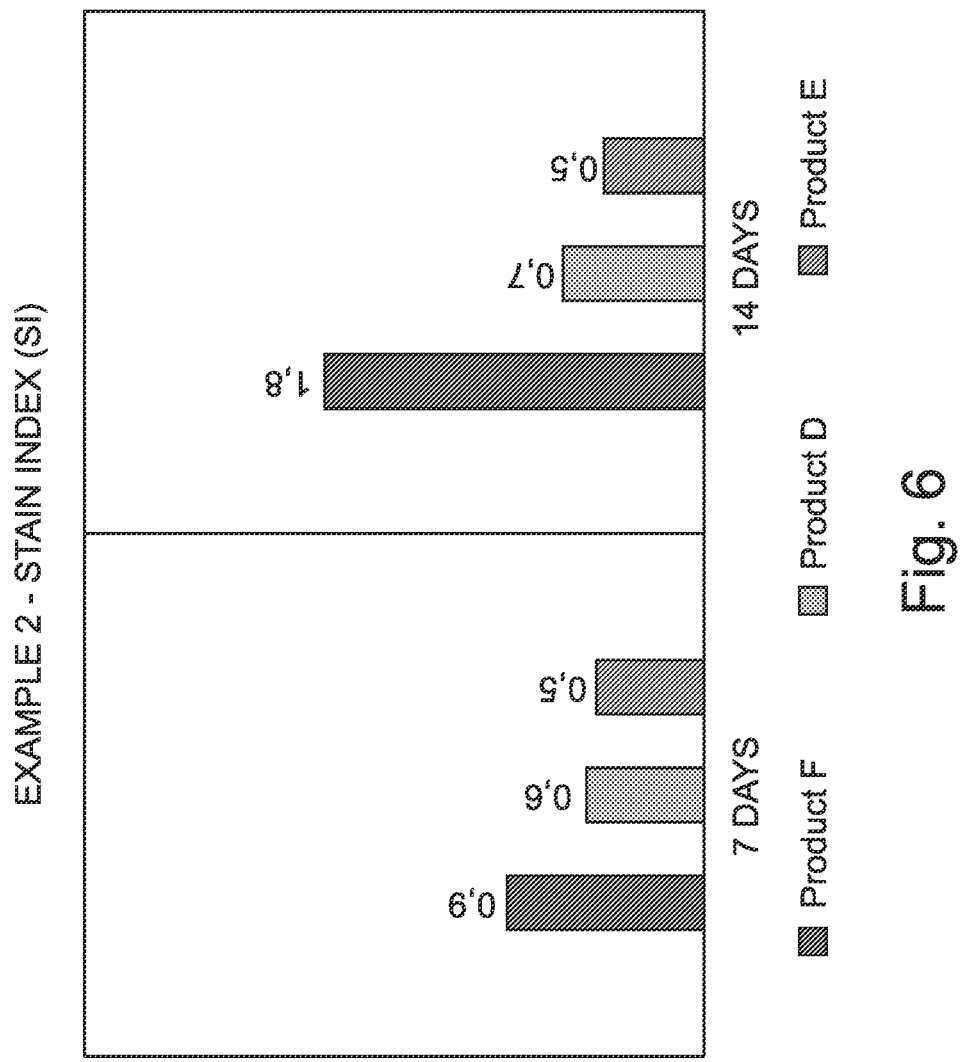
FIG. 6 shows the 7- and 14-day Staining Index (SI) test results for the groups that used products D, E, and F according to Example 2.

Also with regard to the evaluation of the Stain Index (SI), the 3 mouthwashes showed results consistent with those obtained in Example 1 (FIG. 6). The analysis relative to the average values showed a lower tendency to pigmentation of tooth surfaces after the treatment cycles with Products D and E, compared to those with control mouthwash (Product F). The difference, already present after 7 days, is even more marked after 14 days of treatment.

In addition thereto, the tendency already highlighted in Example 1, of a lower tendency to develop pigmentation in the group of patients treated with Product E could be confirmed, which allowed to highlight how the use of N-acetyl cysteine allows to increase the effect of the ADS system with sodium metabisulfite and ascorbic acid in counteracting tooth pigmentation in patients undergoing chlorhexidine treatment.

Example 3

Goal of the Study

The aim of this study was to evaluate with a larger group of subjects, the efficacy of a 0.2% chlorhexidine mouthwash and the anti-staining ADS system (0.5% by weight of sodium metabisulfite, 0.5% by weight of ascorbic acid) designed to counteract the onset of dental stains and compare it with an innovative mouthwash having the same composition but with an additional 0.5% by weight of N-acetyl cysteine. As a control group, a traditional mouthwash was used with 0.2% chlorhexidine, but without sodium metabisulfite, ascorbic acid, or N-acetyl cysteine.

Materials and Methods

At the IRCCS Galeazzi structure in Milan and at 2 freelance dental practices in Milan and Cinisello Balsamo, 60 male and female patients, aged between 19 and 31, were selected on a voluntary basis, in accordance with the principles of the Helsinki Declaration. The 60 patients were undergoing antiseptic therapy with suspension of oral hygiene manoeuvres after surgery or extraction, periodontal or implant therapies. Subjects with serious systemic pathologies, such as cardiovascular diseases, diabetes, neurological or psychiatric syndromes, or infectious diseases and who declared allergies to the components of the products used, were not included in the trial. Also excluded from the study were patients who were unable to correctly perform home oral hygiene manoeuvres.

After enrolment, 3 types of bottles were prepared for each patient, which were absolutely identical, inert, opaque, with a capacity of 250 ml, into which it was introduced:
  Product A: mouthwash with chlorhexidine at 0.2% by weight containing 0.5% by weight of sodium metabisulfite, 0.5% by weight of ascorbic acid, and 0.01% by weight of sodium DNA, with respect to the total volume of the mouthwash;
  Product B: like Product A, but with the addition of 0.5% by weight of N-acetyl cysteine, with respect to the total volume of the mouthwash; and
  Product C: traditional mouthwash with chlorhexidine at 0.2% by weight with respect to the total volume of the mouthwash.

The bottles, with a neutral label, were then simply marked with an alphanumeric code that uniquely identified the patient to whom it had been assigned, originating from randomization software (Random Allocation Software®). The reading key was kept unknown by the test organizer until the end of the evaluation, in order to prevent the volunteer patient or the operator selected for the evaluations from becoming aware of what type of mouthwash they were testing. The test was then performed according to the "double-blind" criterion.

Prior to the start of the study, all patients underwent professional oral hygiene sessions, in order to remove existing soft and hard plaque deposits and to zero the periodontal indices to be analysed:
  Plaque index (PI), for the amount of plaque present.
  Gingival index (GI), for the level of gum inflammation.
  Stain index (SI), for the extent of pigmentations.
  Plaque Index, Gingival Index, and Stain Index, were analysed according to the same methods used in Example 1.

The 60 patients were divided into 3 groups identical in number and assigned to group A (Product A), to group B (Product B) or to group C (Product C) and each patient was then assigned 2 bottles of the corresponding product, sufficient to cover the entire period of use.

The patients performed a 14-day rinse cycle with the delivered product, as well as regularly prescribed chlorhexidine-based antiseptic therapies. The cycle included a rinse with 15 ml of pure product for one minute, to be performed 2 times a day. During the period of use of the mouthwashes, the patients did not brush or use any other oral hygiene devices. Finally, the patients were asked not to take substances capable of favouring the deposition of pigments, such as coffee, tea, red wine or cigarette smoke, less than an hour before or after rinsing and in any case to report their possible intake during the day by means of a special form to be filled out.

After 7 and 14 days the periodontal parameters PI and GI were then measured, in addition to the SI. After 14 days, the patients resumed normal hygiene procedures if surgical healing had allowed recovery.

All the data were collected by a single examiner in special data folders and then analysed through an analysis program and spreadsheet. The statistical analysis was performed by ANOVA Test for the analysis of variance.

Results

Of the 60 volunteer patients selected and included in the test, 57 completed the study. 2 patients (1 in group A and one in group B) did not show up for the 7-day follow-up and 1 (Group A) on the 14th day.

There were no interruptions to the protocol nor delays in the evaluation sessions. The patients maintained similar dietary regimens during the treatment cycle to which they had been subjected, without substantial differences especially in the intake of the staining substances that they were asked to report on the appropriate sheet delivered.

Figure 7:
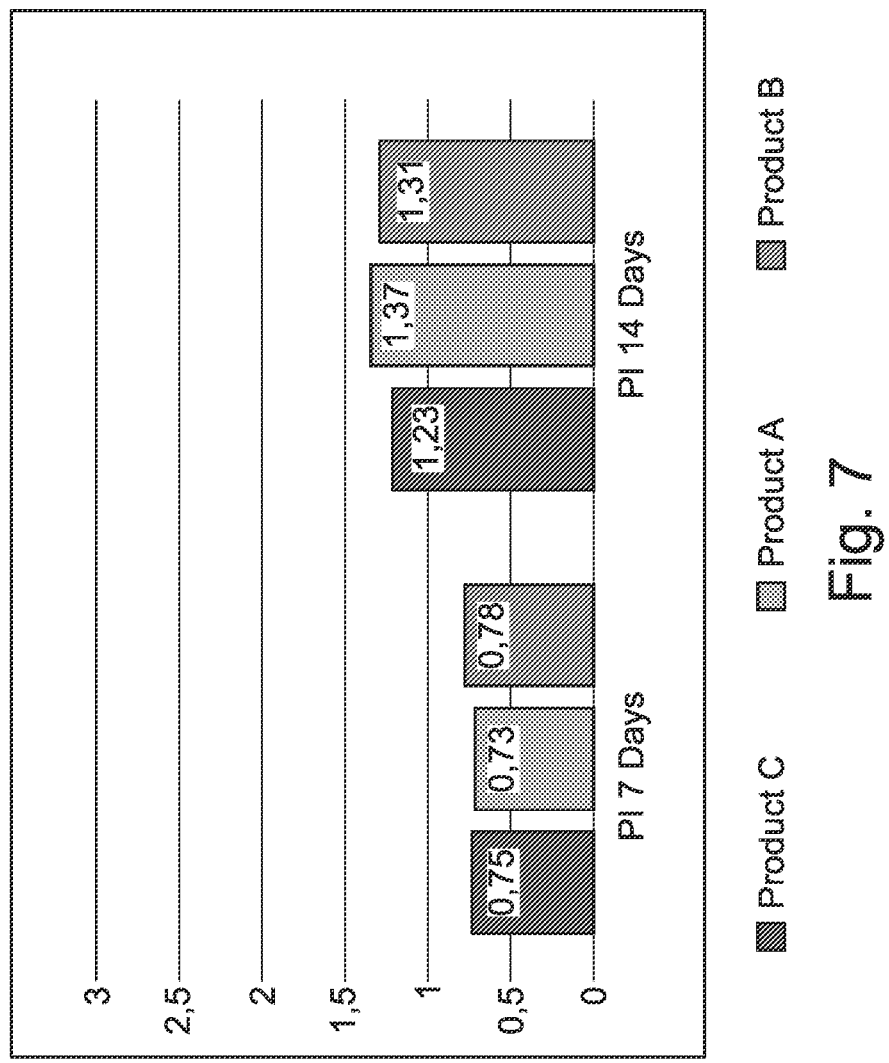
FIG. 7 shows the 7- and 14-day Plaque Index (PI) test results for the groups that used products A, B, and C according to Example 3.
Figure 8:
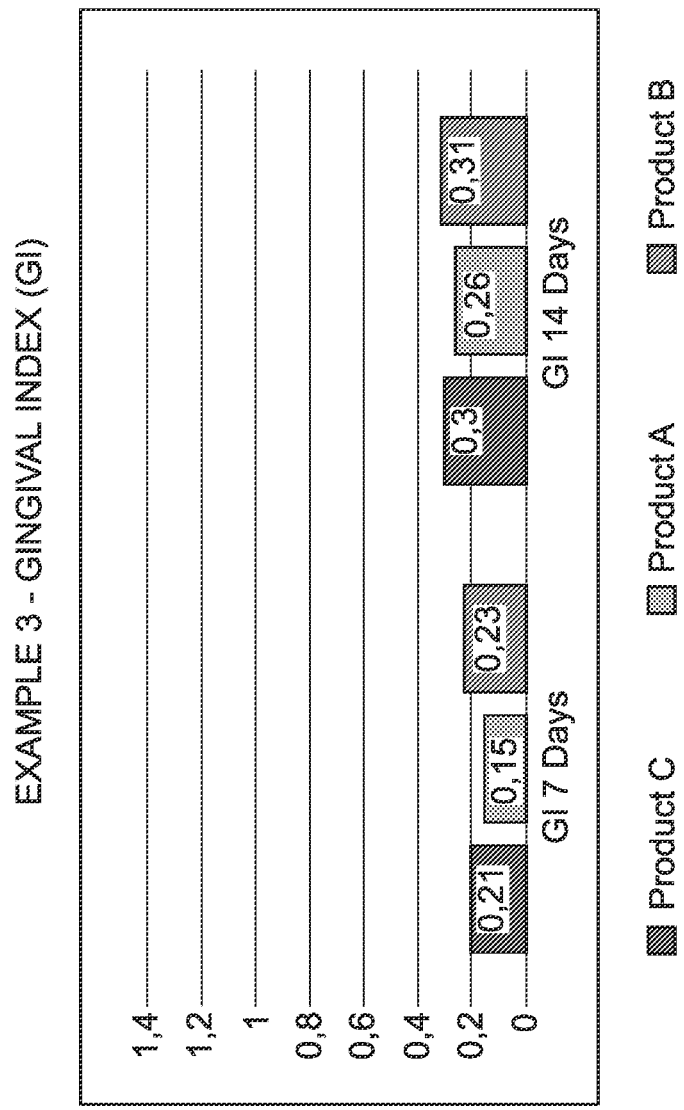
FIG. 8 shows the results of the 7- and 14-day Gingival Index (GI) test for the groups that used products A, B, and C according to Example 3.

In the measurements carried out, the Plaque Index and Gingival Index values showed a similar trend with all types of mouthwashes (FIGS. 7 and 8). This finding confirms the results of the previous tests performed and described in Example 1.

In particular, a progressive plaque accumulation on the tooth surfaces was highlighted in most cases during the observation period, more marked in the presence of surgical sutures and flaps. The evaluation of the amount of plaque with the aid of the periodontal probe showed in fact a mostly invisible accumulation in the first week (PI=0 or 1) and manifested by a periodontal probe in the second week (several subjects with PI=2). However, no statistically significant differences between the three mouthwash formulations emerged from the collected data relating to PI and GI.

Similarly to many other studies involving chlorhexidine, despite the presence of plaque, when analysing the Gingival Index, no particular gingival inflammatory states were appreciated in the three groups, except for mild gingival reddening at a marginal level in a few subjects (GI=1). This figure (FIG. 8) also appears in line with the previous test on the same formulations described in Example 1. However, the recording of the Stain Index (SI) showed significant differences when compared to the previously obtained results of Example 1: the 3 mouthwashes in fact showed a different trend in the development of dental pigmentation, as shown in FIG. 9.

The analysis relating to the mean SI values in fact confirmed an effective anti-pigmentation action for mouthwashes equipped with the ADS system (Products A and B) compared to those with a control mouthwash containing chlorhexidine without ADS (Product C), which was statistically significant both at the 7-day observation and at the 14-day observation.

In fact, it has been known for several years that the ADS component is able to reduce dental pigmentation resulting from the use of an antiseptic with chlorhexidine, without inhibiting its anti-plaque activity. The action of the ADS system can be conditioned by the quantity of chromogenic substances introduced by the subject during the period of use, but good control of the diet and observation of the doctor's prescriptions, together with the anti-pigmenting system, can guarantee an evident anti-stain effect even in conditions of real clinical use. The difference between the SI measurements between the two groups with ADS system (Products A and B) and the one without ADS system (Product C) was statistically significant both at 7 days and at 14 days of treatment. Surprisingly, compared to the test performed in Example 1 on a more limited number of subjects, in this test the mouthwash with ADS/NAC anti-staining system (Product B) showed a tendency to develop less pigmentation which was statistically significant compared to group A even if only after 14 days.

CONCLUSIONS

In the light of what has been collected and analysed, it can be stated that the anti-staining system taken into analysis by this test (Anti Discoloration System, ADS®) and introduced in chlorhexidine mouthwash formulations, confirms the results of the literature (Van Swaaij B W M, et al . . . "Does chlorhexidine mouthwash, with an anti-discoloration system, reduce tooth surface discoloration without losing its efficacy? A systematic review and meta-analysis." Int J Dent Hyg. 2020 February; 18 (1): 27-43) and appears to be effectively active in counteracting the onset of dental pigmentation, when compared with a traditional mouthwash with chlorhexidine.

From the data obtained from this study, the ADS® anti-staining system (Product A) does not seem capable of completely eliminating the problem of dental pigmentation. Dental staining is in fact connected to multiple factors, first of all the adherence to the prescriptions, but also to the behaviour suggested by the doctor after the dental therapies. However, by simply analysing the Stain Index values (FIG. 9), it can be observed that the entity of pigmentation obtained after 14 days of use of mouthwashes with the ADS system remains well below the value 1 (poor pigmentation), while for the traditional mouthwash to CHX with alcohol settled between the value 1 and the value 2 (evident pigmentation), with peaks even beyond the value 2. Moreover, the difference between the SI values between the three mouthwashes is statistically significant in favour of the use of those containing the ADS system (Products A and B) at both 7-day and 14-day observation.

With regard to the introduction of the new NAC component in the mouthwash with the ADS and DNA system (Product B), according to the present invention, it was possible to observe a conservation of the antiseptic efficacy of chlorhexidine and, in parallel, a further reduction in the extent of dental pigmentation at 7 and above all at 14 days. In this test, the difference between mouthwash A (Product A: CHX-ADS-DNA) and mouthwash B (Product B: CHX-ADS-DNA-NAC) was statistically significant in favour of Product B of the invention (the CHX-ADS-DNA-NAC) association just after 14 days of use. Example 1, carried out on healthy volunteers showed a further benefit deriving from the addition of NAC to a mouthwash with Chlorhexidine and ADS system in terms of reduction of dental pigmentation. In the present Example, on the other hand, the difference of dental staining reduction appears more evident, to the point of being significant after 14 days of observation, as previously indicated.

To explain this difference between the results of Examples 1 and 3, some hypotheses were formulated. Firstly, Example 3 was performed on patients who actually underwent dental therapies that required the suspension of oral hygiene procedures: extractions, implant surgery, gum surgery, to name a few. In this case, compared to healthy volunteers (Example 1), the patients may have been much more inclined to observe the recommendations and, above all, may have given up on the temptation to brush their teeth, which is not really verifiable when healthy volunteers are involved in the studies. The greater accumulation of plaque and, consequently, of chromogens could have amplified the benefits of anti-staining systems, especially in those areas that need it most, such as those with surgical wounds and sutures. The already significant number of patients included (Group A=28, Group B=29, Group C=30) as well as the nature of patients actually clinically undergoing surgical therapies (and not healthy volunteers as in Example 1) make this test particularly interesting: it seems confirm that the combination of an ADS system, already known in the literature, with N-Acetyl-Cysteine (NAC) can under clinical conditions enhance the anti-staining action of ADS alone, with further benefits in terms of patient compliance and good results of therapies.

The invention claimed is:

1. An oral care product comprising chlorhexidine, at least one metabisulfite salt of an alkali or alkaline earth metal, ascorbic acid, and N-acetyl cysteine.

2. The oral care product according to claim 1, wherein the chlorhexidine is in the form of a salt or a complex.

3. The oral care product according to claim 1, comprising sodium DNA.

4. The oral care product according to claim 1, selected from the group consisting of: mouthwash, periodontal gel, and toothpaste.

5. The oral care product according to claim 4, wherein said product is a mouthwash and the amount of chlorhexidine ranges from 0.01% to 0.30% by weight with respect to the total volume of the mouthwash.

6. The oral care product according to claim 5, wherein said product is a mouthwash and the amount of the at least one metabisulfite salt of an alkali or alkaline earth metal ranges from 0.1% to 0.5%, with respect to total volume of the mouthwash.

7. The oral care product according to claim 6, wherein said product is a mouthwash and the amount of ascorbic acid ranges from 0.1% to 1.0% by weight, with respect to the total volume of the mouthwash.

8. The oral care product according to claim 7, wherein said product is a mouthwash and the quantity of N-acetyl cysteine ranges from 0.01% to 1.0% by weight, with respect to the total volume of the mouthwash.

9. The oral care product according to claim 8, wherein said product is a mouthwash comprising from 0.01% to 0.30% by weight of chlorhexidine, from 0.1% to 0.5% by weight of at least one salt metabisulfite of an alkali or alkaline earth metal, from 0.1% to 1.0% by weight ascorbic acid, from 0.01% to 1.0%, by weight of N-acetyl cysteine, from 0.01% to 0.2% by weight of sodium DNA, from 0.05% to 1% by weight of at least one polyvinyl pyrrolidone-vinyl acetate copolymer, with respect to the total volume of the mouthwash.

10. The oral care product according to claim 4, wherein said product is a periodontal gel comprising from 0.5% by weight to 1.0% by weight of chlorhexidine, with respect to the total volume of the periodontal gel.

11. The oral care product according to claim 10, wherein said product is a periodontal gel and the amount of N-acetyl cysteine ranges from 0.01% to 1.0% by weight, with respect to the total volume of the periodontal gel.

12. The oral care product according to claim 4, wherein said product is a toothpaste comprising from 0.05% by weight to 0.2% by weight of chlorhexidine, with respect to the total volume of the toothpaste.

13. The oral care product according to claim 12, wherein said product is a toothpaste and the amount of N-acetyl cysteine ranges from 0.01% to 1.0% by weight, with respect to the total volume of the toothpaste.

14. Method of treating at least one pathology selected from the group consisting of: gingivitis, bacterial plaque and periodontitis in a patient in need thereof with the oral care product according to claim 13, said method comprising
administering to said patient a pharmaceutical effective amount of said oral care product.

* * * * *